(12) United States Patent
Shimasaki et al.

(10) Patent No.: US 11,325,130 B2
(45) Date of Patent: May 10, 2022

(54) MULTIWELL INSTRUMENT

(71) Applicants: GINREILAB INC., Ishikawa (JP);
SHINKO CHEMICAL CO., LTD.,
Ishikawa (JP)

(72) Inventors: Takeo Shimasaki, Ishikawa (JP);
Yumiko Kitano, Ishikawa (JP); Hideki Yamada, Ishikawa (JP)

(73) Assignees: GINREILAB INC., Ishikawa (JP);
SHINKO CHEMICAL CO., LTD.,
Ishikawa (JP)

( * ) Notice: Subject to any disclaimer, the term of this patent is extended or adjusted under 35 U.S.C. 154(b) by 147 days.

(21) Appl. No.: 16/076,854

(22) PCT Filed: Feb. 10, 2017

(86) PCT No.: PCT/JP2017/004969
§ 371 (c)(1),
(2) Date: Aug. 9, 2018

(87) PCT Pub. No.: WO2017/138648
PCT Pub. Date: Aug. 17, 2017

(65) Prior Publication Data
US 2019/0046978 A1     Feb. 14, 2019

(30) Foreign Application Priority Data
Feb. 12, 2016 (JP) .............................. JP2016-025282

(51) Int. Cl.
*B01L 3/00* (2006.01)
*C12M 1/12* (2006.01)
*C12Q 1/02* (2006.01)
*G01N 1/00* (2006.01)
(Continued)

(52) U.S. Cl.
CPC ......... *B01L 3/5085* (2013.01); *B01L 3/50855* (2013.01); *C12M 23/12* (2013.01);
(Continued)

(58) Field of Classification Search
CPC ............... B01L 3/5085; B01L 3/50855; B01L 2200/0647; B01L 2200/028;
(Continued)

(56) References Cited

U.S. PATENT DOCUMENTS 5,578,490 A    11/1996   Martinez Ubeira
5,602,028 A    2/1997   Minchinton
(Continued)

FOREIGN PATENT DOCUMENTS

CN     102703318     10/2012
JP      10-262649      10/1998
(Continued)

OTHER PUBLICATIONS

Japanese Office Action dated Nov. 6, 2019 in Japanese Patent Application No. 2017-567016 with Machine Translation.
(Continued)

*Primary Examiner* — Michael L Hobbs
(74) *Attorney, Agent, or Firm* — Wenderoth, Lind & Ponack, L.L.P.

(57) ABSTRACT

A multiwell instrument includes a vessel having an inside; a plurality of culture plates arranged in the inside of the vessel, each individual one of the plurality of culture plates having an inside in which material to be examined can be stored; and filters disposed inside the respective culture plates to partition the insides of the respective culture plates into at least two wells which are horizontally adjacent.

10 Claims, 8 Drawing Sheets

(51) Int. Cl.
*C12M 1/00* (2006.01)
*C12M 1/32* (2006.01)

(52) U.S. Cl.
CPC ............ *C12M 23/34* (2013.01); *C12M 25/04* (2013.01); *C12Q 1/02* (2013.01); *G01N 1/00* (2013.01); *B01L 2200/028* (2013.01); *B01L 2200/0647* (2013.01); *B01L 2300/0681* (2013.01); *B01L 2300/0829* (2013.01)

(58) Field of Classification Search
CPC .... B01L 2300/0681; B01L 2300/0829; C12M 25/04; C12M 23/12; C12Q 1/02; G01N 1/00
See application file for complete search history.

(56) References Cited

U.S. PATENT DOCUMENTS

| | | | |
|---|---|---|---|
| 5,882,922 A | | 3/1999 | Tyndorf et al. |
| 5,962,250 A | * | 10/1999 | Gavin ................ B01L 3/5025 422/552 |
| 2005/0101010 A1 | | 5/2005 | Li |
| 2016/0369224 A1 | | 12/2016 | Shimasaki et al. |

FOREIGN PATENT DOCUMENTS

| | | | | |
|---|---|---|---|---|
| JP | 2007-510429 | | 4/2007 | |
| JP | 2007-215472 | | 8/2007 | |
| JP | 2010-051200 | | 3/2010 | |
| JP | 2015-213497 | | 12/2015 | |
| WO | 2011/161480 | | 12/2011 | |
| WO | WO-2011161480 A1 | * | 12/2011 | ............ B01L 3/5085 |
| WO | 2013/116449 | | 8/2013 | |
| WO | 2015/009893 | | 1/2015 | |
| WO | 2015/019938 | | 2/2015 | |
| WO | 2017/134464 | | 8/2017 | |
| WO | 2018/009870 | | 1/2018 | |

OTHER PUBLICATIONS

International Search Report dated Mar. 7, 2017 in International (PCT) Application No. PCT/JP2017/004969.
Extended European Search Report dated Feb. 6, 2020 in European Patent Application No. 17750369.5.
Partial Supplementary European Search Report dated Sep. 23, 2019 in corresponding European Patent Application No. 17750369.5.

* cited by examiner (A)

(B)

FILTER 6

MULTIWELL INSTRUMENT

TECHNICAL FIELD

The present invention relates to a multiwell instrument including a plurality of wells for culturing objects such as cells, organs and microorganisms, or storing the objects to be used as a part of an inspecting apparatus.

BACKGROUND ART

Conventionally, as a laboratory instrument with which a large number of specimens can be observed and inspected at a time, there has been a microtiter plate (micro plate). A microtiter plate is an instrument in a flat-plate shape in which a large number of wells are formed, and makes it possible to place cells, microorganisms or the like to be inspection objects in the respective wells, and culture or inspect the cells, microorganisms or the like under different conditions in the respective wells. By using a microtiter plate, objects to be inspected in the large number of wells can be easily compared at a time.

However, in the conventional microtiter plate, the respective wells are independent, and do not share a culture medium, so that it is difficult to use the conventional microtiter plate for the purpose of inspecting an interaction among different objects to be inspected (for example, cell strains derived from different organs) or the like.

As another inspection tool, Transwell sold by Corning Incorporated or the like may be cited, but since it is necessary to perform an operation of detaching and attaching the insert portion, there is a tendency that time and labor are required more than expected.

SUMMARY OF INVENTION

Technical Problem

The present invention has been made in the light of the above described fact, and an object of the present invention is to provide a multiwell instrument that can extend a use method in a conventional microtiter plate.

Solution to Problem

In order to solve the above described problem, a multiwell instrument of the present invention includes a plurality of wells, and a filter that is disposed between at least one well of the plurality of wells and a well adjacent to the well.

According to the present invention, by providing the multiwell instrument including the plurality of wells and the filter disposed in accordance with a use purpose, it becomes possible to extend a use method of the conventional microtiter plate.

The multiwell instrument of the present invention can be used to culture any biomaterial such as a cell, an organ, and a microorganism. The kind of biomaterial is not specially limited.

The filter is preferably a filter that does not allow a predetermined substance to pass through. For example, the predetermined substance is a biomaterial which is cultured such as a cell, cannot pass through the filter, and therefore, cannot move to the adjacent well. On the other hand, the filter desirably allows a specific substance secreted from the biomaterial to pass through.

That is, whereas the filter does not allow the biomaterial which is cultured to pass through, the filter is desirably allows only the specific substance secreted from the biomaterial to pass through. Since the filter has this property, it becomes possible to move only the substance secreted from the biomaterial through the filter to the adjacent well, in a state where the biomaterial stays in the well. Then, it becomes possible to observe properties (for example, influence that is given to the other cell existing in the adjacent well and the like) of the substances secreted from the biomaterials, without bringing the biomaterials such as cells in the adjacent wells into contact with each other.

A hole diameter of the filter is properly selectable in accordance with the kind of the specific substance secreted from a biological specimen which is cultured, the biomaterial of interest.

For example, in order to prevent the biological specimen from passing through, when the biological specimen which is cultured is a cell, the hole diameter of the filter is preferably 1.2 μm or less, and more preferably 0.6 μm or less. For example, in the case of a human pancreatic cancer cell in culture, the hole diameter is 1.2 μm or less.

For example, when a biological specimen which is cultured is an organ, the hole diameter of the filter is preferably 5 μm or less, and more preferably 3 μm or less. For example, in the case of a blood cell (erythrocyte), the hole diameter is 5 μm or less.

For example, when the biological specimen which is cultured is a microorganism, the hole diameter of the filter is preferably 0.1 μm or less, and more preferably 0.01 μm or less. For example, in the case of a yeast cell, the hole diameter is 0.1 μm or less. A filter of a hole diameter of 30 μm or less can be properly used for bacteria (0.2 to 30 μm), a filter of a hole diameter of 100 μm or less can be properly used for pollen (10 to 100 μm), and a filter of a hole diameter of 3 μm or less can be properly used for a poliovirus (2.37 μm), respectively.

A "substance secreted from the biomaterial" is, for example, cytokine, exosome, protein or the like. When the substance secreted from the biological specimen is cytokine, the hole diameter of the filter is preferably 100 μm or less, and in the case of exosome, the hole diameter is 0.03 μm or less. In the case of protein, the hole diameter is 0.1 μm or less, and a filter of a hole diameter corresponding to a substance size of protein is further used.

As other examples, in the case of inorganic salt, glucose, vitamin B12, insulin, aprotinin, dextran, cytochrome, myoglobin, hemoglobin, and bovine serum albumin, a filter of a hole diameter of 0.01 μm or less can be properly used. A filter of a hole diameter of 0.02 μm or less can be properly used for IgG (0.018 μm), a filter of a hole diameter of 0.07 μm or less can be properly used for IgM (0.065 μm), a filter of a hole diameter of 0.2 μm or less can be properly used for pyrogen (0.003 to 0.2 μm), a filter of a hole diameter of 0.1 μm or less can be properly used for a virus (0.005 to 0.1 μm), a filter of a hole diameter of 0.1 μm or less can be properly used for carbon black (0.01 to 0.1 μm), and a filter of a hole diameter of 1 μm or less can be properly used for pigment (0.01 to 1 μm), respectively. It is also possible to use commercially available filters.

On the other hand, in order to allow the substances to pass through, filters of hole diameters of sizes larger than the aforementioned hole diameters are used. By properly using these filters, change in the observation phenomenon according to presence or absence of passage of the substance can be seen. Note that the combinations of the biomaterials and substances, and the hole diameters of the filters for use in these biomaterials and substances are only examples, and the present invention is not limited to the combinations disclosed in the above description, and can be arbitrarily changed in accordance with the various conditions and variation of the object size.

As one aspect, it is also possible to use a semipermeable membrane as the filter. For example, a membrane that adsorbs a specific substance, or on the contrary, a membrane that does not adsorb a specific substance can be used.

In order to cope with various use purposes, at least some of the plurality of wells are classified into a plurality of groups, and a filter may be disposed between wells that are adjacent in a same group so that wells in the same group communicate with each other. Further, a filter is not provided between a well of one group and a well which is of another group and is adjacent to the well, and thereby it becomes possible to provide the present invention to various use purposes.

For example, each of the plurality of wells includes an upper opening portion, a bottom surface, and an inner wall portion formed between the upper opening portion and the bottom surface. An area of the bottom surface is preferably smaller than an area of the upper opening portion. Further, the inner wall portion includes at least an upper section and a lower section, the lower section is closer to the bottom surface than the upper section, and a cross-sectional area of the lower section is smaller than a cross-sectional area of the upper section.

Further, the multiwell instrument further includes a through-hole extending between the upper section of the inner wall portion and an upper section of an inner wall portion of an adjacent well, and the filter may be disposed in the through-hole.

For example, the upper section of the inner wall portion is in a rectangular shape, and the lower section is in a cylindrical shape. Further, the bottom surface is preferably a transparent or dark circular region, for example.

In a preferable aspect, the plurality of wells are arranged in two or more rows and two or more columns.

Further, the multiwell instrument of the present invention includes a body integrally formed, and the plurality of wells are recessed portions of the body. The body may be transparent, and may be in a flat-plate shape.

In another aspect of the multiwell instrument of the present invention, the body includes at least one culture plate, and the filter is disposed inside the culture plate so as to partition an inside of the culture plate into at least two of the wells. The filter is preferably contained in a filter frame. In the other aspect, a plurality of the culture plates are included, and the body may further include a vessel in which a plurality of the culture plates are arranged.

A method according to one aspect of the present invention is for performing screening of a biomaterial by using the above described multiwell instrument.

A method according to another aspect of the present invention is for performing screening of a substance secreted from a biomaterial by using the above described multiwell instrument.

A method according to still another aspect of the present invention includes the steps of disposing a biomaterial in one of two adjacent wells in the above described multiwell instrument, disposing a filter that allows a first substance secreted from the biomaterial to pass through, between the two wells, and disposing a second substance that is chemically bound to the first substance, in the other one of the two wells. In the present aspect, it is possible to perform screening by setting the two adjacent wells as a pair, and using the above described multiwell instrument in which a plurality of the pairs are arranged.

BRIEF DESCRIPTION OF DRAWINGS

FIG. 5(A) illustrates an example in which a cross-sectional area of a well inner wall portion continuously decreases toward a bottom surface, and FIG. 5(B) illustrates an example in which a cross-sectional area decreases in three steps or more.

DESCRIPTION OF EMBODIMENTS

Hereinafter, respective embodiments of the present invention will be described with reference to the drawings.

First Embodiment

FIG. 1 to FIG. 5 illustrate a multiwell instrument I according to a first embodiment of the present invention, and with use of these drawings, a configuration of the multiwell instrument I will be described first.

Figure 1:
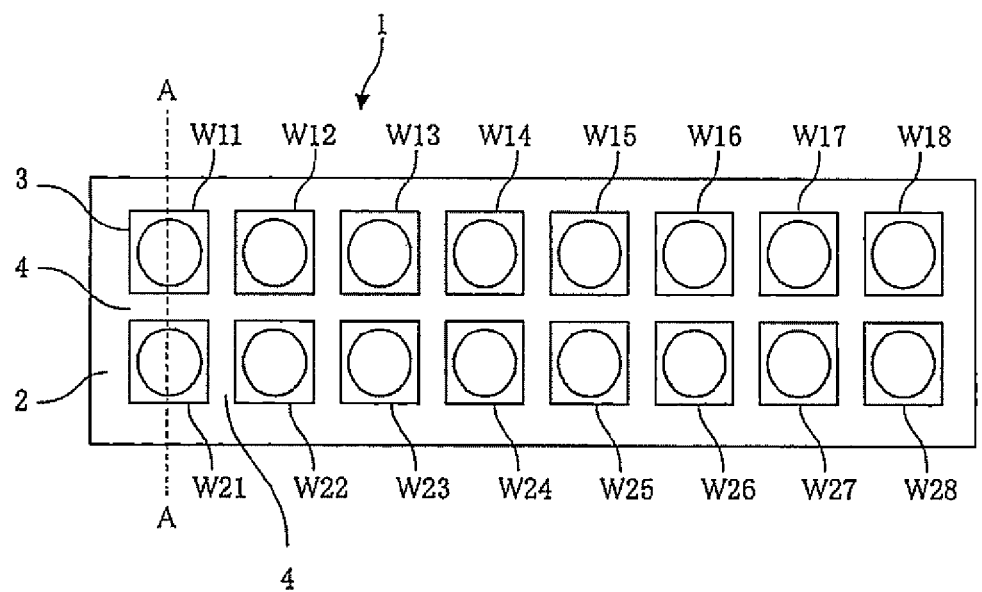
FIG. 1 is a plan view of a multiwell instrument according to a first embodiment of the present invention.

As illustrated in a plan view of FIG. 1, the multiwell instrument 1 has a plurality of wells 3 formed in a body 2 in a flat-plate shape. Between the respective wells and adjacent wells, boundary portions 4 are formed to separate the wells respectively. As illustrated in a bottom view of FIG. 2, in the multiwell instrument 1, circular bottom surfaces 10 are formed on bottom portions of the respective wells.

The body 2 may be made of plastics, glass or the like, but is not limited to these materials. Further, the body 2 may be made of a colorless or colored transparent material, but can be made of a nontransparent material. Further, the body 2 can be made by integral molding with all of the boundary portions 4. As a matter of course, the body 2 also can be made by combining several components. Further, it is also possible to make the boundary portions 4 from a colorless or colored transparent material, or a colored nontransparent material.

In an example illustrated in the drawing, the wells 3 are formed in two rows and in eight columns. Here, the well 3 in an i row and in a j column is expressed as W1j (i=1 to 2, j=1 to 8).

Figure 3:
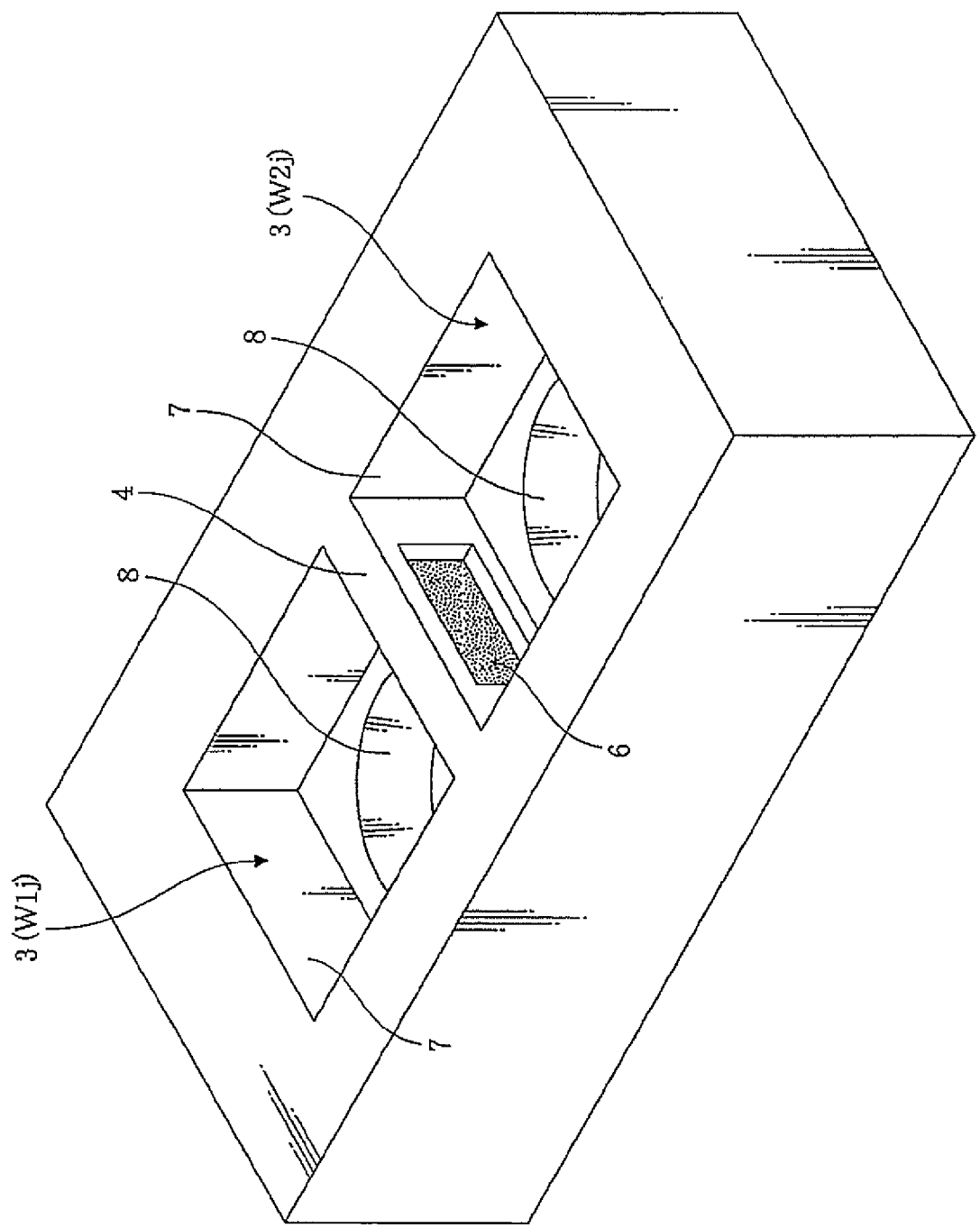
FIG. 3 is a perspective view of two adjacent wells included by the multiwell instrument illustrated in FIG. 1.
Figure 4:
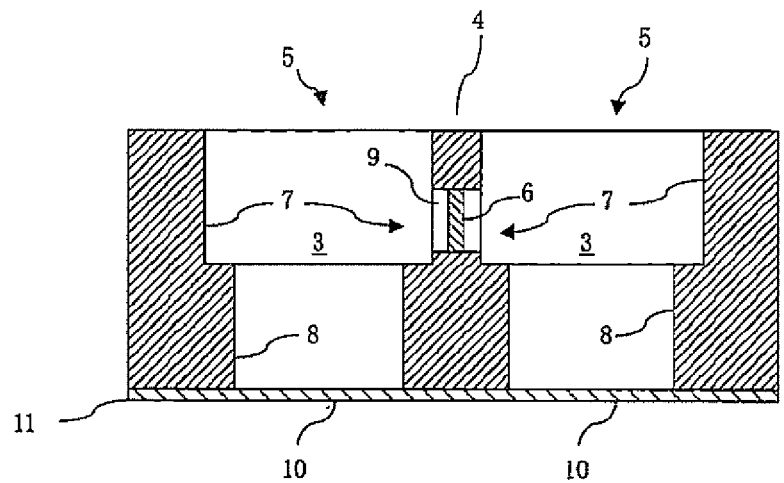
FIG. 4 is a sectional view taken along line A-A of the adjacent wells constituting the multiwell instrument illustrated in FIG. 1.
Figure 5:
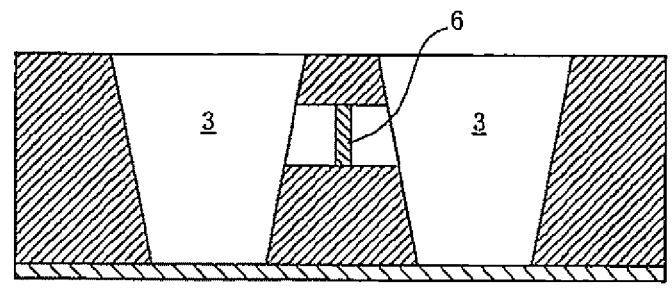
FIG. 5 is a view illustrating other examples of a sectional configuration of the wells.
Figure 5:
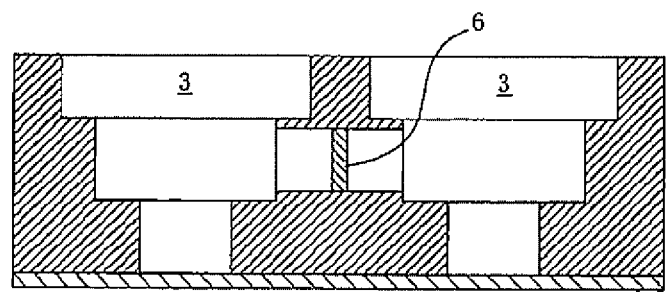

FIG. 3 illustrates a perspective view of two wells W1j and W2j adjacent in the same column. Further, FIG. 4 illustrates a sectional view of the multiwell instrument 1 taken along line A-A in FIG. 1. Note that line A-A in FIG. 1 passes through the wells W11 and W21, and sectional shapes are also the same in combinations of other two adjacent wells (W1j, W2j).

As illustrated in FIG. 3, in the boundary portion 4 of the two wells W1j and W2j which are adjacent in the same column, a filter 6 is provided. Further referring to FIG. 4 here, the well 3 includes an upper opening portion 5, a bottom surface 10, and an inner wall portion (7, 8) formed between the upper opening portion 5 and the bottom surface 10. The inner wall portion includes an upper section 7 in a rectangular shape provided at an upper opening portion 5 side, and a lower section 8 in a cylindrical shape provided at a bottom surface 10 side, and a cross-sectional area of the lower section 8 is formed to be smaller than a cross-sectional area of the upper section 7. Note that in order to discriminate a kind of the filter 6 and presence or absence of the filter, colors of the boundary portions 4 can be respectively made different colors, and can be made different colors from the other part of the body 2.

As illustrated in FIG. 4, a through-hole 9 that provides communication between the upper section 7 of the well W1j and the upper section 7 of the well W2j is formed in the boundary portion 4 between the wells W1j and W2j, and the filter 6 is attached to the through-hole 9. As the filter 6, for example, a filter that does not allow an object of a predetermined size or more such as a cell to pass through, but allows a liquid and secretions of the cell to pass through can be selected.

When a specimen in the well is observed by using an optical microscope or the like, the bottom surface 10 is preferably made transparent. In this case, by irradiating light from the transparent bottom surface, it becomes easy to observe the specimen in the well. In contrast to this, when fluorescence in the well is observed, it becomes possible to facilitate observation by making the bottom surface 10 a dark color (black).

Figure 2:
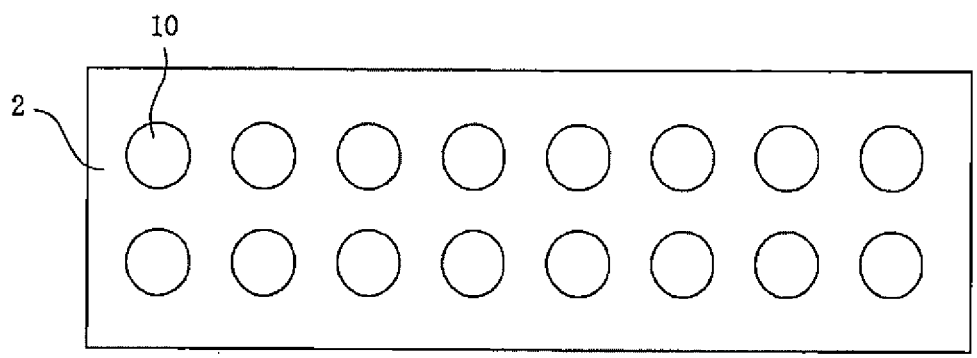
FIG. 2 is a bottom view of the multiwell instrument illustrated in FIG. 1.

For example, the bottom surface 10 of the well 3 can be made transparent by forming the bottom surface of the well 3 as an opening portion at first, and joining a transparent plate 11 such as glass over an entire bottom surface of the multiwell instrument 1. When the lower section 8 is in a cylindrical shape, the bottom surface 10 of the well 3 is also circular as illustrated in FIG. 2. As a matter of course, the transparent plate 11 may be molded integrally with the body 2. In this case, transparency of the bottom surface 10 can be made higher than transparency of the other part.

When a cell is cultured in the well 3, a sufficient volume of supernatant can be stored in an upper region of the well 3 and allowed to penetrate into the adjacent well through the filter 6, by making the cross-sectional area of the lower section 8 smaller than the cross-sectional area of the upper section 7. On the other hand, the volume is small in a lower region of the well 3, so that it becomes possible to prevent a culture solution from being increased more than necessary as a whole. Further, it becomes possible to form an area of the bottom surface 10 to be smaller than an area of the upper opening portion 5, and there is provided a merit that an inspection substance adhering to the bottom surface 10 can be easily observed, for example, as compared with the case where the bottom surface 10 is formed to have the same area and shape as the upper opening portion 5. That is, when the bottom surface 10 is formed into a circular shape, portions at four corners are cut as compared with the rectangular bottom surface, so that it becomes possible to perform observation without being affected by the substances which are accumulated at the corners.

Other than the shape of the inner wall portion of the well 3 illustrated in FIGS. 3 and 4, various other shapes are conceivable in exhibiting the above described operational effects. As the other shapes like this, for example, as illustrated in FIG. 5(A), a shape in which a cross-sectional area is decreasing continuously from the upper opening portion 5 to the bottom surface 10 is cited. Further, as illustrated in FIG. 5(B), the inner wall portion 3 of the well 3 may be formed of three sections in which a cross-sectional area is decreasing discretely toward the bottom surface 10. It is needless to say that the inner wall portion may be formed of four or more sections without being limited to the three sections.

The multiwell instrument of the present invention is suitable for culturing a biomaterial such as a cell. A plurality of wells are included, and in particular, the filters are provided between the respective wells and adjacent wells, so that only a culture medium is shared by the wells connected by the filter without bringing biomaterials in the adjacent wells into direct contact with each other. By using the filter that allows a specific substance, for example, a specific substance secreted from a biomaterial to pass through, it becomes possible to investigate an influence of the specific substance on the biomaterial in the adjacent well, for example.

Next, a use method of the multiwell instrument 1 according to the first embodiment will be described specifically.

According to the multiwell instrument 1 according to the first embodiment, the filter 6 is provided in the boundary portion 4 of the two wells W1j and W2j (j=1, 2, . . . 8) adjacent in the same column. As an example, it is assumed that different cells $C_1$ and $C_2$ (not illustrated) are cultured respectively in the two wells W1j and W2j, and as the filter 6, a filter is used, which allows a secretion substance $X_1$ of the cell $C_1$ and a secretion substance $X_2$ of the cell $C_2$ to pass through, but does not allow the cells $C_1$ and $C_2$ to pass through.

When the cells $C_1$ and $C_2$ are cultured respectively in the respective wells W1j and W2j, the secretion substances $X_1$ and $X_2$ are released from the respective cells. The cells $C_1$ and $C_2$ cannot pass through the filter 6, and are relatively heavy, so that the cells $C_1$ and $C_2$ are distributed in vicinities of the bottom portions of the wells, and parts of the cells accumulate on the bottom surfaces 10. On the other hand, the secretion substances $X_1$ and $X_2$ disperse in the respective wells, and parts of the secretion substances reaching upper portions of the wells as supernatants pass through the filter 6 to penetrate into the adjacent well. That is, the secretion substance $X_1$ penetrates into the well W2j, and the secretion substance $X_2$ penetrates into the well W1j.

The penetrated secretion substances $X_1$ and $X_2$ disperse in the respective adjacent wells, and reach the cells $C_2$ and $C_1$ in the adjacent wells. The cells $C_2$ and $C_1$ can be affected by the secretion substances $X_1$ and $X_2$ from the different cells under the environment in which they are placed. In this way, it becomes easy to investigate an interaction of the different cells by observing the respective cells accumulated on the bottom surfaces 10 of the wells W1j and W2j which are adjacent in the same column.

Further, by changing the kind of cells, and properly changing the condition such as the kind of culture solution for each column (j=1, 2, . . . 8), it becomes possible to grasp a difference in interaction between the cells for each kind of cell and for each condition, at a time.

As described above, it is possible to use the instrument in screening a biomaterial having a specific property, or a substance having a specific property.

As another use method, it is possible to change a hole diameter of the filter 6, and allow the secretion substance $X_1$ of the cell $C_1$ to pass through, but not to allow the secretion substance $X_2$ of the cell $C_2$. In this case, the secretion substance $X_1$ can penetrate into the well $W2j$ and affect the cell $C_2$, but the secretion substance $X_2$ cannot penetrate into the well $W1j$ and affect the cell $C_1$. This makes it possible to identify a causative factor of the interaction between the cells $C_1$ and $C_2$.

In the case where it is unknown which secretion substance affects cells, or the like, the hole diameter of the filter 6 is changed at each column j=1, 2, . . . 8), and the kind of the secretion substance that can pass through is changed at each column, whereby which secretion substance affects cells in what manner can be easily identified.

As still another use method, a use method is possible, that puts a cell in only one of the two adjacent wells, and does not put a cell in the other well. In this case, as the filter 6, a filter that allows a specific secretion substance which is an object to be inspected to pass through is used. The substance secreted from the cell passes through the filter 6, moves to the adjacent well, and adheres to the bottom surface 10 of the adjacent well. It becomes possible to quantify the secretion substance adhering to the bottom surface 10.

As a specific example of the still other use method described above, it is possible to use the multiwell instrument of the present invention in an enzyme-linked immunosorbent assay (ELISA: Enzyme-Linked ImmunoSorbent Assay). ELISA generally treats a cell extract, a supernatant or the like, thereafter adds the cell extract, the supernatant or the like to what is made by sticking antibody to a plate bottom surface (a so-called ELISA plate), and quantifies the cell extract or the like by using properties of the antibody and a coloring substance. In the present invention, an ELISA function may be put into one of the two wells connected by the filter, for example. The substance secreted from the cell passes through the filter to reach the other well, where a protein or the like can be quantified.

An antibody is generally coated (adheres) onto the bottom surface 10 of plastics easily, and in general, a primary antibody is caused to adhere to an entire surface. In this case, a measured substance bound to the antibody generally glows dimly. As the amount of the measured substance is large, the bound amount is also large, and the measured substance which is bound is not removed even in a cleaning process, and is resultantly measured as a signal with high intensity. In one aspect of the present invention, with an objective of measuring transition in a natural process, the cleaning process may not be performed. In that case, a fine magnet or iron is fixed to only a part of the bottom surface, and the other parts are made less susceptible to adherence of antibodies. It is possible to provide a mechanism that causes magnetic beads to adhere to the antibody side, and thereby antibodies adhere to only a specific part. Note that a method for causing antibodies to adhere to only a part of the bottom surface is not limited to the above described example, but other methods may be used.

Second Embodiment

In the first embodiment, the instrument in which the wells are arranged in two rows and in eight columns, and the filter is provided in each of the boundary portions of the two wells adjacent in the same columns is described. However, the cases are conceivable, in which an interaction among three or more different cells is inspected, in which the number of conditions that are changed for each column is larger than eight, and in which the number of conditions which are changed for each column may be smaller than eight.

Figure 6:
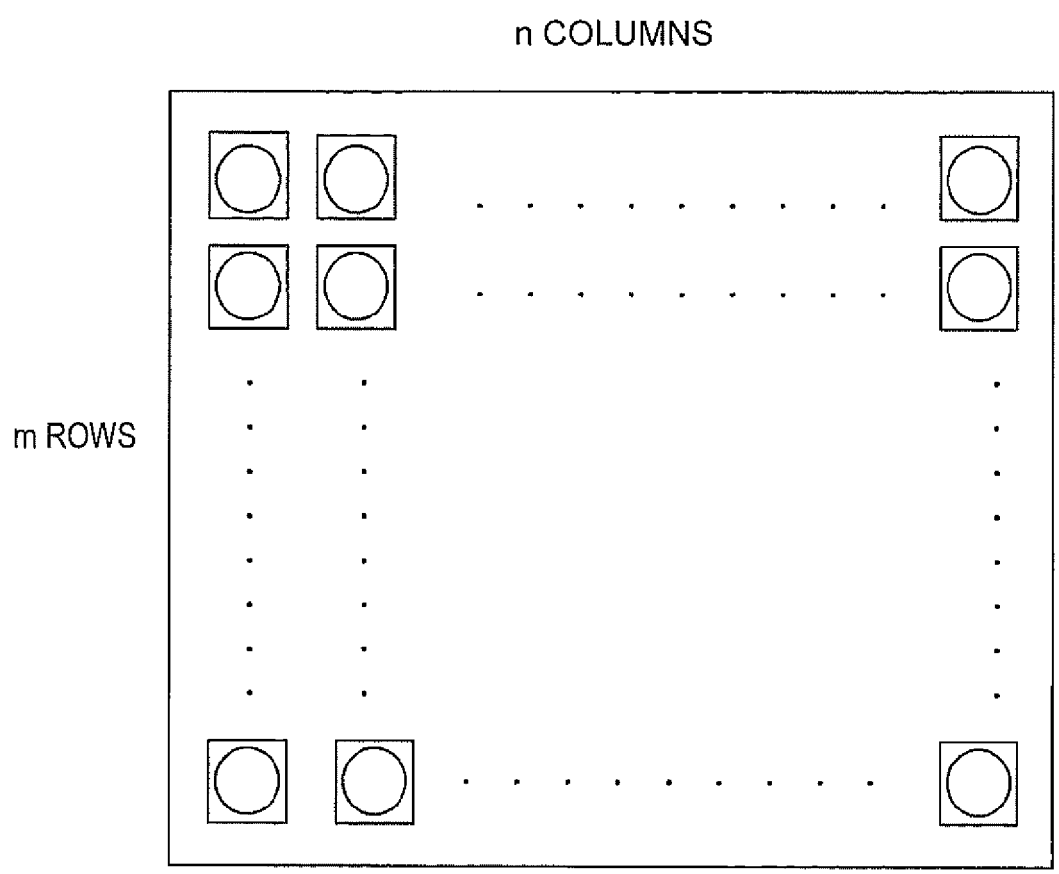
FIG. 6 is a plan view of a multiwell instrument in which a plurality of wells are arranged in an arbitrary matrix of m×n, according to a second embodiment of the present invention.

Therefore, a second embodiment provides an instrument in which wells are arranged in m rows and n columns (m≥2, n≥2), which is more generalized, as illustrated in FIG. 6. In this case, an instrument of a minimum configuration is an instrument in which wells are arranged in two rows and two columns (m=2, n=2). Well arrangements with two rows and 16 columns (m=2, n=16), with four rows and 10 columns (m=4, n=10), and with 12 rows and eight columns are also preferable aspects. Arrangement with two rows and eight columns which corresponds to the first embodiment is also preferable.

In the second embodiment, an instrument in which wells are arranged in optimal numbers of rows and columns in accordance with an inspection object can be selected.

Further, in the second embodiment, an instrument in which the filter 6 is provided in a certain boundary portion of boundary portions among arbitrary adjacent wells is provided. For example, in the case of the instrument of the well arrangement with two rows and 16 columns, the second embodiment includes not only the case where the filter is provided in the boundary portion between the wells in different rows and in the same column, but also the case where the filter is also provided in the boundary portion between two wells adjacent in the same row, as in the first embodiment.

Accordingly, in the second embodiment, in accordance with disposition of the filter, a group of the wells communicating with each other through the filter can be properly selected in accordance with a use object.

Figure 7:
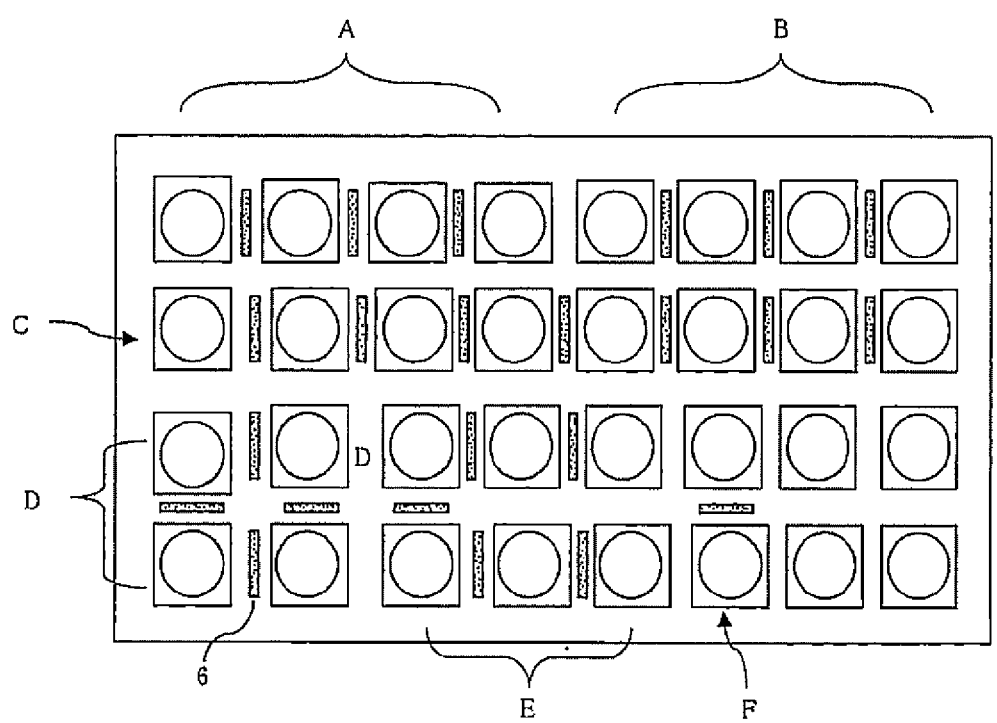
FIG. 7 is a plan view of the multiwell instrument illustrating an example of arrangement of the wells constituting each of a plurality of groups in the multiwell instrument in FIG. 6.

FIG. 7 illustrates disposition columns of the filters 6 in an instrument of well arrangement with four rows and eight columns (m=4, n=8). Note that in FIG. 7, reference sign of the well is $W1j$ (i denotes a row number, j denotes a column number) as in the first embodiment. In this case, a well in an upper left corner is denoted by W11, and a well in a lower right corner is denoted by W48.

In the instrument illustrated in FIG. 7, the filters 6 are provided between adjacent wells in wells W11, W12, W13 and W14 which are arranged in a first row to form group A. Further, the filters 6 are provided between adjacent wells in wells W15, W16, W17 and W18 which are arranged in the same first row to form group B. In either group A or group B, a specific substance that passes through the filters 6 penetrates into the four wells from one another, so that for example, when different cells are cultured respectively in the respective wells, it becomes possible to study an interaction among four kinds of cells.

Further, as in group C, the filters 6 may be provided between adjacent wells in all of wells W21, W22, . . . , W28 which are arranged in the second row. In this case, it becomes possible to study an interaction among eight kinds of cells.

Further, not only the wells which continue in the same rows (or columns) are made the objects which are caused to communicate with one another as in groups A to C, but also the filters 6 may be provided in all of boundary portions between wells (W31, W32, W41, W42) which are adjacent in different rows and different columns as in group D.

Furthermore, as an aspect of causing wells across two or more rows and columns to communicate with one another, there is an aspect like group E. That is, in group E, not only a group of wells (W33, W34, W35) which continue in a certain row, and a group of wells (W43, W44, W45) which continue in a different row are caused to communicate with one another in the same rows, but also the filter is provided in the boundary portion between the wells W33 and W43. Thereby, it becomes possible to cause six wells in total to communicate with one other through the filters.

In group F, the filter is provided between two wells (W36, W46) which are adjacent in the same column. As a matter of course, an aspect of causing three or more wells in the same column to communicate with one another is also conceivable.

Further, like wells W37, W38, W47 and W48, independent wells which are not provided with filters between the wells and adjacent wells also can be disposed. Thereby, it becomes possible to use cells which are not affected by secretion substances from the other cells as comparison objects, or it becomes possible to use some of the wells which are formed in the instrument according to the present embodiment like the conventional multititer plate.

Third Embodiment

In the second embodiment, the instrument in which the disposition of the filters 6 is set in advance is provided.

Figure 8:
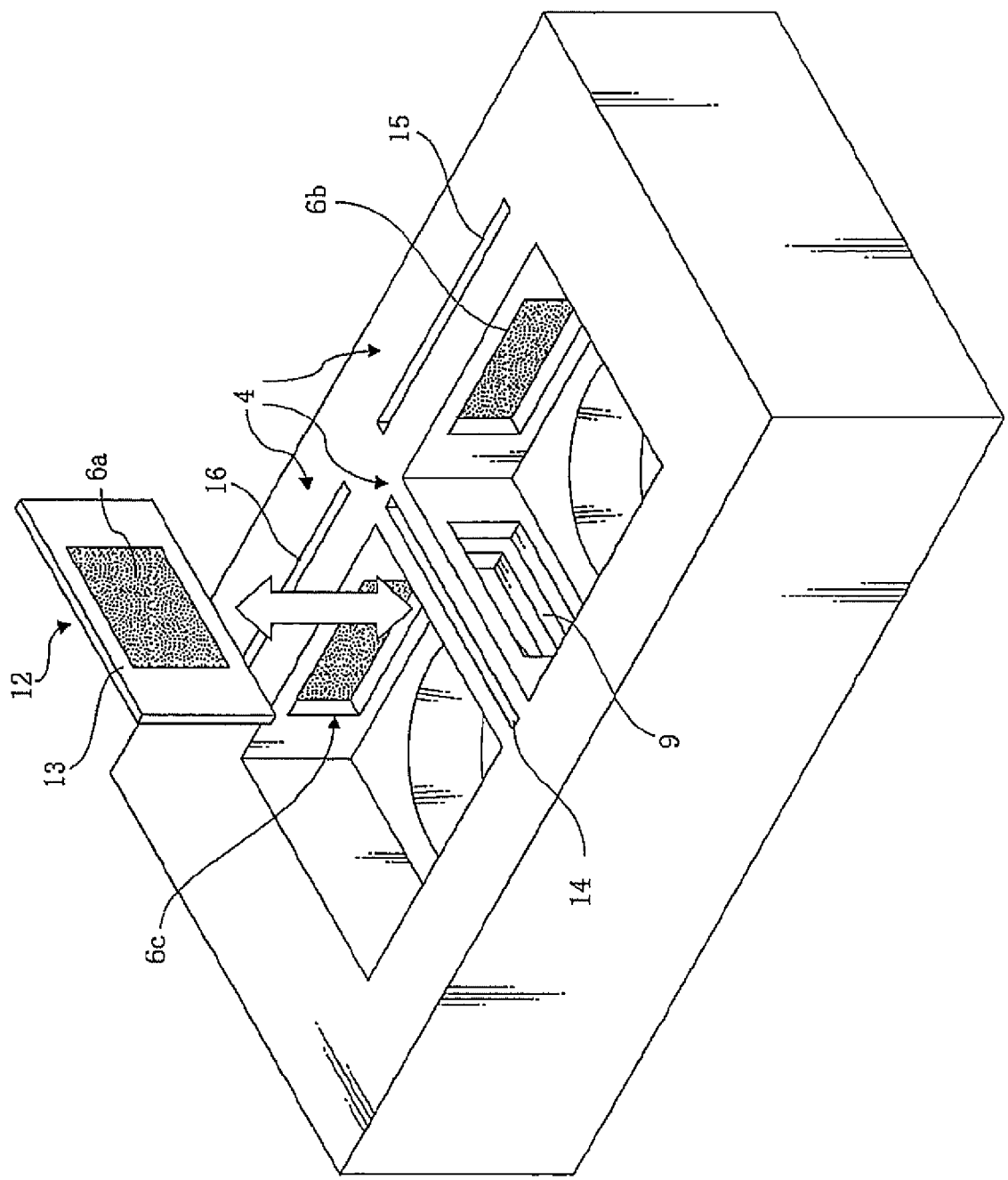
FIG. 8 is a perspective view of two adjacent wells included by a multiwell instrument according to a third embodiment which is capable of exchanging a filter.

In the third embodiment, in order to make it possible to dispose the filters 6 detachably and attachably, slits in which the filters are insertable are provided in the boundary portions of the wells which are adjacent in the same rows and the same columns, in the multiwell instrument in FIG. 7. For example, as illustrated in FIG. 8, slits 14, 15 and 16 are provided in the respective boundary portions 4, and filter frames 12 are inserted in these slits.

The filter frames 12 are capable of being inserted in and detached from the slits 14, 15 and 16, and each includes a filter 6a and a seal portion 13. When the filter frame 12 is inserted in each of the slits 14, 15 and 16, the filter 6a is contained in a through-hole 9 which penetrates through the adjacent wells, and the seal portion 13 hermetically closes a space between the through-hole 9 and the filter frame 12.

When the adjacent wells are shut off, a frame which is not provided with the filter is inserted in the slit between the wells which are desired to be shut off. Further, it is also possible to make filters that are inserted in other slits 15 and 16 filters 6b and 6c (filters with different hole diameters, for example) which are different from the filter 6a.

According to the third embodiment, it becomes possible to dispose an arbitrary filter in the arbitrary well boundary portion 4, so that it becomes possible to provide the multiwell instrument which enables various use methods as illustrated in FIG. 7.

In the example of FIG. 8, the example is shown in which the slit is provided between the two adjacent wells, and the filter frame 12 includes one filter. The third embodiment is not limited to the example, but also includes a mode of providing a single slit that extends throughout boundary portions of a plurality of well columns which are arranged, and a single filter frame that includes a plurality of filters which are inserted in the slit.

Further, the third embodiment also includes a mode in which slit are present in some of the boundary portions, instead of all of the boundary portions.

Fourth Embodiment

In the above described embodiment, the example in which the filter 6 is disposed inside the boundary portion 4 is shown, but a mode in which only a filter is disposed in adjacent wells or a mode in which a filter and a frame of the filter are disposed is also within the scope of the present invention. That is, a mode in which at least some of the boundary portions 4 have only the filters 6, or only the filters 6 and the frames of the filters 6 is possible. Further, as the well, a mode except for the well formed in the body 2 as described above is also possible.

Figure 10:
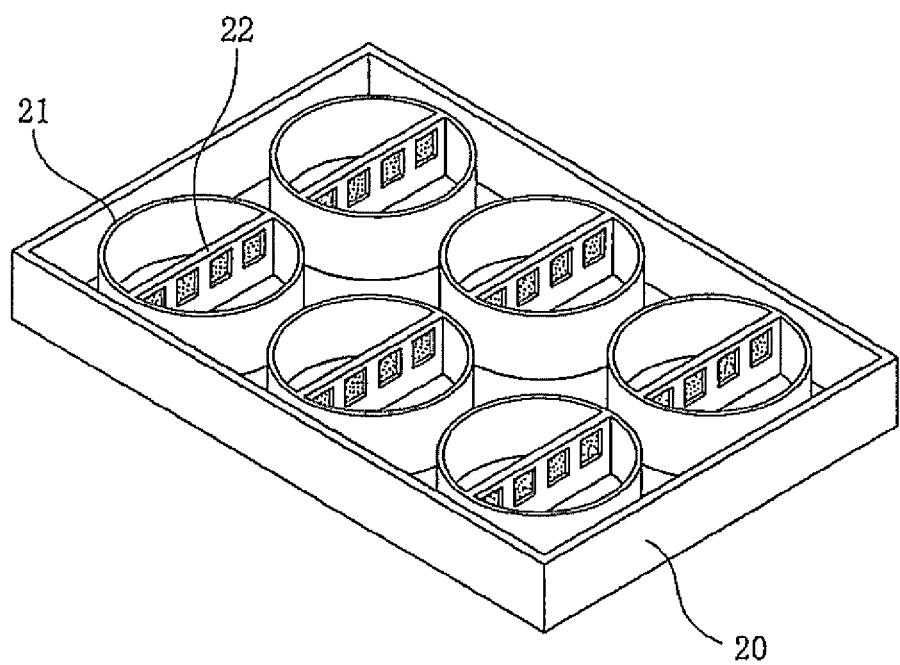
FIG. 10 is a perspective view illustrating a multiwell instrument according to a fourth embodiment.

An example of the above modes is illustrated in FIG. 10 as a fourth embodiment.

As illustrated in FIG. 10, the multiwell instrument according to the fourth embodiment has a configuration in which a plurality of culture plates 21 are arranged inside a base vessel 20. By disposing a filter frame 22 loaded with filters is disposed in each of the culture plates 21, two wells are formed in each of the culture plates 21. A so-called "circular culture plate" that is generally used is also usable as the culture plate 21.

There are various modified examples in the fourth embodiment, and a multiwell vessel that uses, for example, the single culture plate 21 independently without using the base vessel 20 is also possible. Further, a size and a shape of the culture plate 21 may be variously changed, and the culture plates 21 which are arranged in the single base vessel 20 may have shapes other than the circular culture plate, or different shapes and size respectively.

Further, the filter frame 22 may be formed so that a filter is disposed at a higher position as in the boundary portion 4 illustrated in FIG. 4. Furthermore, it is also possible to form the filter frame so that the filter frame 22 partitions an inside of the single culture plate 21 into three or more wells, and a whole of the filter frame 22 may be configured as a filter.

The above is the embodiments of the present invention, but the present invention is not limited to the above described embodiments, and can be changed arbitrarily and properly within the scope intended by the present invention.

For example, in the arrangement of the wells with m rows and n columns illustrated in FIG. 6 or the like, the wells are arranged in a straight line in the same rows or in the same columns, but the present invention is not limited to the arrangement like this. A mode in which the wells are not arranged in a straight line in the same rows and the same columns, for example, a mode in which the wells are disposed by being alternately shifted from each other is also included in the scope of the present invention.

Further, the present invention is not limited to the examples disclosed in the specification and the drawings as for the shape of the well 3. For example, the upper opening portion 5 and the upper section 7 of the well are described as in a rectangular shape, but are not limited to this shape, and can take any other form such as a polygonal column and a cylindrical shape. Further, the lower section 8 of the well is described as in a circular column shape, but is not limited to this shape, and can take any other form such as a polygonal column.

Figure 9:
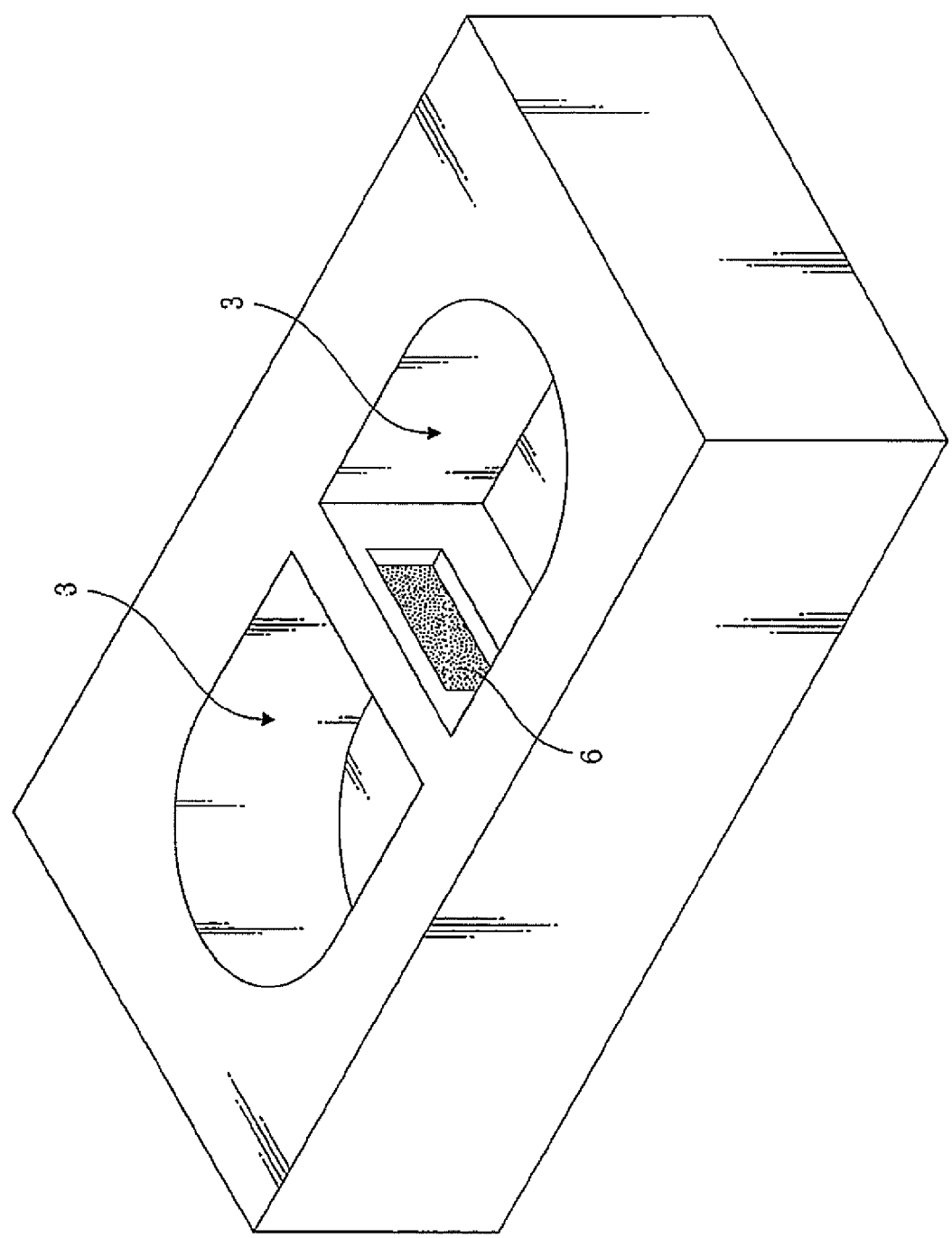
FIG. 9 is a perspective view illustrating a modified example of a well.

Further, in the above described example, the sectional shapes and the sectional areas in the upper section and the lower section of the well are made different, but the present invention is not limited to this, and the sectional shapes and the sectional areas of the upper section and the lower section may be made the same. For example, as illustrated in FIG. 9, all the sections of the wells may be semicircular. As a matter of course, the well may appropriately have a section in any shape surrounded by a closed curved line such as a circle and an oval, any polygonal shape or the like. Further, the case where the sectional shapes are the same but the sectional areas are different up and down, and the case where the sectional areas are the same but the sectional shapes are different up and down are also included in the scope of the present invention.

Further, in the fourth embodiment illustrated in FIG. 10, the respective culture plates 21 are not separately formed, but are formed as holes formed in the body as in the embodiment illustrated in FIG. 2, and the filter frames 22 may be disposed in the respective holes.

Further, the filter 6 is described as rectangular, but the filter 6 is not limited to this shape, but can have any shape such as a semicircle, a circle, a triangle, and a polygon. Further, the shape of the bottom surface 10 is not limited to a circular shape, and the bottom surface 10 in a shape such as a polygon is also included in the scope of the present invention.

Further, the body 2 of the multiwell instrument 1 is described as the body in a flat-plate shape, but a body formed into a column shape by increasing the depth of the well 3 is also within the scope of the present invention.

Furthermore, the use method of the multiwell instrument 1 is not limited to the disclosed contents. For example, the use method of the multiwell instrument 1 described in the first embodiment is also applicable in the second and third embodiments.

REFERENCE SIGNS LIST

1 Multiwell instrument
2 Body
3 Well
4 Boundary portion
5 Upper opening portion
6, 6a, 6b, 6c Filter
7 Upper section (inner wall portion)
8 Lower section (inner wall portion)
9 Through-hole
10 Bottom surface
11 Transparent plate
12 Filter frame
13 Seal portion
14, 15, 16 Slit
20 Base vessel
21 Culture plate
22 Filter frame

The invention claimed is:

1. A multiwell instrument comprising:
a vessel having an inside;
a plurality of culture plates arranged in the inside of the vessel, each individual one itself of the plurality of culture plates having an inside in which biomaterial to be cultured and examined can be stored; and
boundary portions disposed inside the respective culture plates to partition the insides of the respective culture plates into at least two wells which are horizontally adjacent,
wherein each of the boundary portions comprises a filter with a hole diameter of 5 µm or less, and a step is formed between a surface of the boundary portion and a surface of the filter,
wherein the filter is configured: (i) not to allow the biomaterial to pass through; and (ii) to allow a specific substance secreted from the biomaterial to pass through, and
wherein each of the boundary portions and each of the culture plates in which each of the boundary portions is disposed are molded into a single piece.

2. A method for performing screening of a biomaterial by using the multiwell instrument according to claim 1.

3. A method for performing screening of a substance secreted from a biomaterial by using the multiwell instrument according to claim 1.

4. A method comprising:
disposing a biomaterial in a first of two adjacent wells in the multiwell instrument according to claim 1;
disposing one of the filters that is configured to allow the specific substance secreted from the biomaterial to pass through, between the two adjacent wells, wherein the specific substance is a first substance; and
disposing a second substance that is able to chemically bind to the first substance in a second of the two adjacent wells.

5. The method according to claim 4, wherein screening is performed by setting the two adjacent wells as a pair, and using the multiwell instrument in which a plurality of the pairs are arranged.

6. A multiwell instrument comprising:
a vessel having an inside;
a plurality of culture plates arranged in the inside of the vessel, each individual one itself of the plurality of culture plates having an inside in which biomaterial to be cultured and examined can be stored; and
boundary portions disposed inside the respective culture plates to partition the insides of the respective culture plates into at least two wells which are horizontally adjacent,
wherein each of the boundary portions comprises a filter,
wherein the filter is configured: (i) not to allow the biomaterial to pass through; and (ii) to allow a specific substance secreted from the biomaterial to pass through, and
wherein the culture plates are spaced apart inside the vessel such that there is an empty space or void between each adjacent pair of the culture plates.

7. A method for performing screening of a biomaterial by using the multiwell instrument according to claim 6.

8. A method for performing screening of a substance secreted from a biomaterial by using the multiwell instrument according to claim 6.

9. A method comprising:
disposing a biomaterial in a first of two adjacent wells in the multiwell instrument according to claim 6;
disposing one of the filters that is configured to allow the specific substance secreted from the biomaterial to pass through, between the two adjacent wells, wherein the specific substance is a first substance; and
disposing a second substance that is able to chemically bind to the first substance in a second of the two adjacent wells.

10. The method according to claim 9, wherein screening is performed by setting the two adjacent wells as a pair, and using the multiwell instrument in which a plurality of the pairs are arranged.

* * * * *